United States Patent
Beerstecher

(10) Patent No.: US 6,866,507 B2
(45) Date of Patent: Mar. 15, 2005

(54) FOOT SWITCH

(75) Inventor: Lutz Beerstecher, Borex (CH)

(73) Assignee: Ferton Holding S.A. (CH)

( * ) Notice: Subject to any disclaimer, the term of this patent is extended or adjusted under 35 U.S.C. 154(b) by 113 days.

(21) Appl. No.: 10/104,395

(22) Filed: Mar. 21, 2002

(65) Prior Publication Data

US 2002/0137007 A1 Sep. 26, 2002

(30) Foreign Application Priority Data

Mar. 23, 2001 (DE) .......................................... 101 14 333

(51) Int. Cl.[7] .............................. A61C 1/02; H01H 3/14
(52) U.S. Cl. ..................................... 433/101; 200/86.5
(58) Field of Search ........................ 433/101; 200/86.5; 318/551

(56) References Cited

U.S. PATENT DOCUMENTS

| | | | | |
|---|---|---|---|---|
| 4,041,609 A | | 8/1977 | Bresnahan et al. ............. 32/22 |
| 4,114,275 A | | 9/1978 | Jones et al. ..................... 32/22 |
| 4,417,875 A | * | 11/1983 | Matsui ........................ 433/101 |
| 4,558,194 A | * | 12/1985 | Wiblin ..................... 200/61.89 |
| 5,214,360 A | * | 5/1993 | Gonser et al. .............. 318/551 |
| 5,340,953 A | * | 8/1994 | Krebs et al. ................ 200/86.5 |
| 5,712,460 A | * | 1/1998 | Carr et al. .................. 200/86.5 |
| 5,837,952 A | * | 11/1998 | Oshiro et al. ............. 200/86 R |
| 6,179,829 B1 | | 1/2001 | Bisch et al. .................... 606/1 |
| 6,450,886 B1 | * | 9/2002 | Oishi et al. .................... 463/36 |

FOREIGN PATENT DOCUMENTS

| | | |
|---|---|---|
| DE | A S1 276780 | 9/1964 |
| DE | 2724051 | 12/1978 |
| DE | 3105875 A1 | 2/1981 |
| DE | 3105875 | 9/1982 |
| DE | 29702436 U1 | 2/1997 |
| DE | 19743524 | 10/1998 |

* cited by examiner

Primary Examiner—Todd E. Manahan
(74) Attorney, Agent, or Firm—Ostrolenk, Faber, Gerb & Soffen, LLP

(57) ABSTRACT

A foot switch for operation of at least two different functional members of a dental apparatus which is operatively connected with the foot switch has at least two press switches which are each formed as a diaphragm switch comprising a printed circuitry with an arrangement between two carrier foils which as a package are supported on a base plate of the foot switch within a hollow formed by an overlaid cover plate and connected by a signalling line with at least two different functional members of the dental apparatus for transmitting functional control signals upon depression of the cover plate.

17 Claims, 2 Drawing Sheets

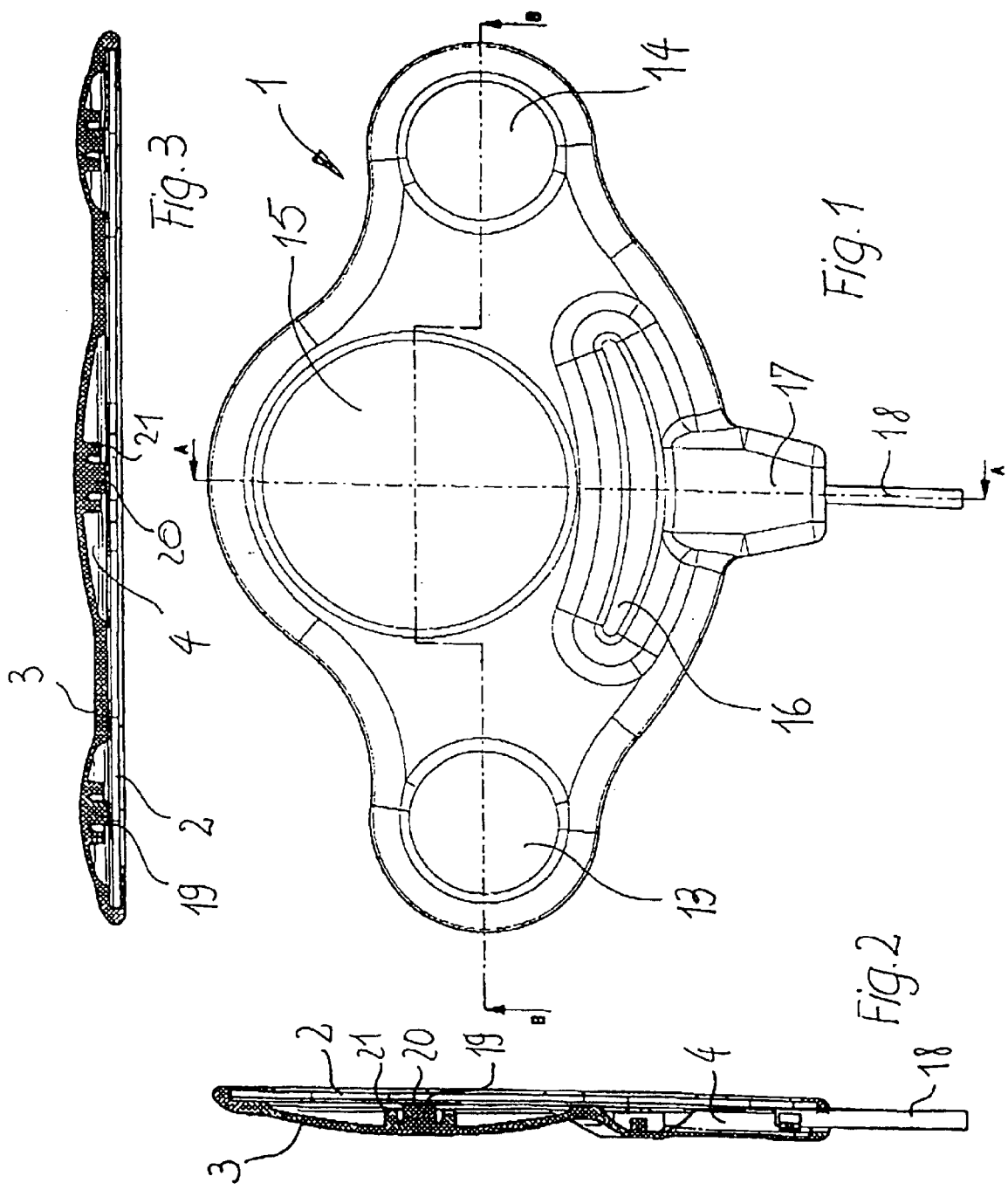

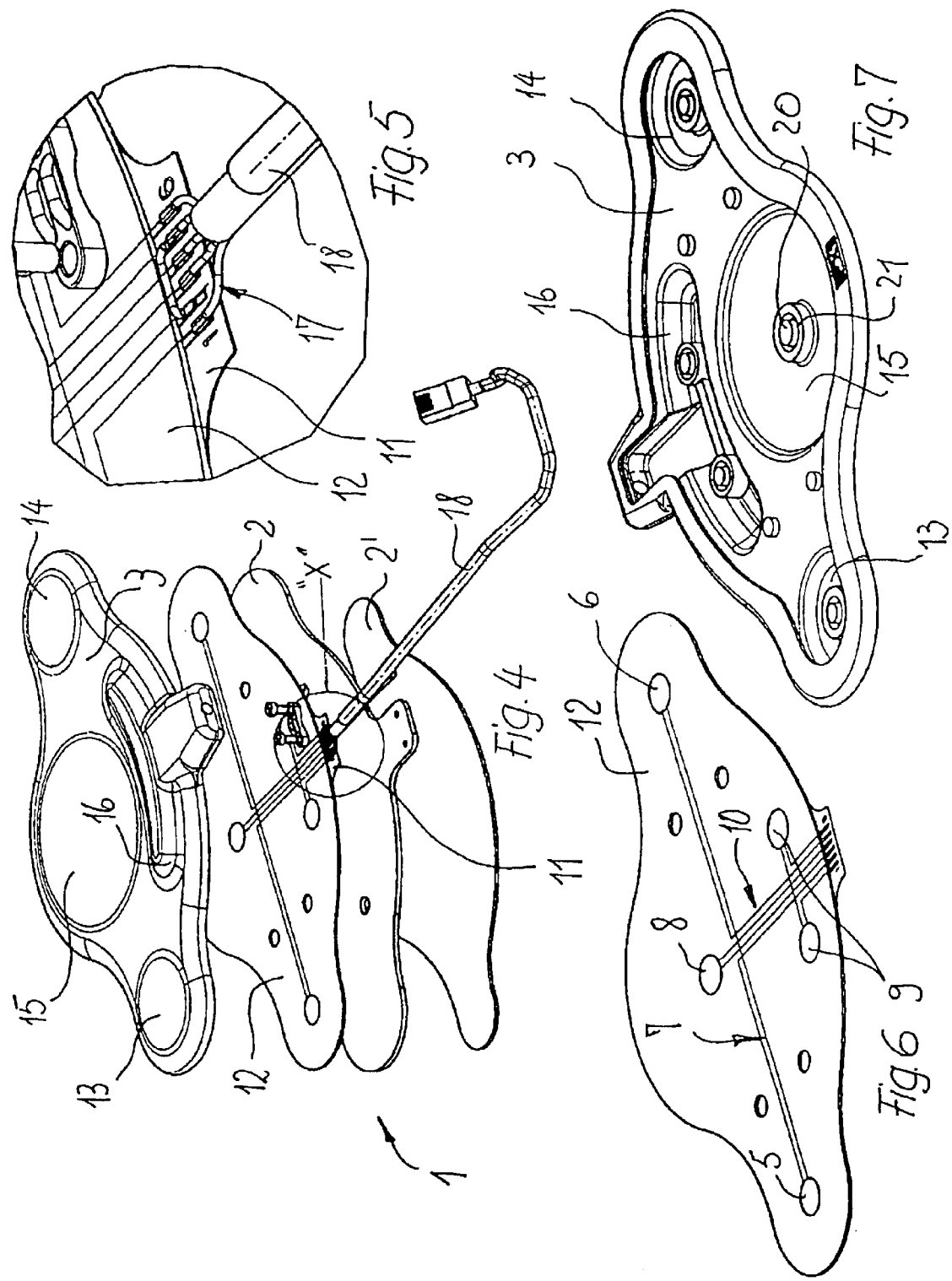

FOOT SWITCH

FIELD OF THE INVENTION

The present invention relates to a foot switch for operation of at least two different functional members of a dental apparatus which is operatively connected with the foot switch.

BACKGROUND OF THE INVENTION

A prior art foot switch of the kind as herein referred is described in U.S. Pat. No. 4,114,275. The foot switch is designed as a relatively flat body which has a circular base plate for supporting the foot switch on the floor at a location close to a dental apparatus. A diaphragm is fixedly connected with the base plate in a fluid-tight manner for providing a hollow which serves as a pneumatic pressure chamber of a variable volume. The diaphragm is covered with a circular cover plate which is relatively moveable to the base plate and biased upwardly by a central pressure spring. By depressing the cover plate the hollow which is surrounded by the diaphragm will be reduced in size against the biasing force of the pressure spring. A pneumatic pressure signal is thereby produced which is transmitted by a signalling line to pneumatic switch valves of the dental apparatus for providing different functional control signals for controlling different functional members of the dental apparatus. The functional members could also comprise an electronic control circuit which is pneumatically actuated with an input switch.

German Patent Application published in DE 31 05 875 A1 discloses a box-shaped foot switch which comprises four pedals that are moveable relatively to a rectangular base plate and arranged in pairs of different size for selectively controlling to dental instruments and adjustable members of a patients chair. The pedals are connected via a logical circuit with a control circuit for the instruments and with a further control circuit for the adjustable members of the patients chair. The box shape of the foot switch results in a minimal trip safety and provides an unfavourable accessibility of the pedals which are arranged in pairs side-by-side so that the actuation of the same is not optimized.

SUMMARY OF THE INVENTION

An object of the present invention is to provide a foot switch which may be designed as flat as possible for avoiding any trip danger and for guaranteeing at the same time a safe functional actuation even of multiple functional members of a dental apparatus which are connected by a signalling line with the foot switch.

The present invention accordingly provides a foot switch which is characterised by the features as outlined in the claims.

A foot switch according to the present invention provides by its at least two press switches which are each formed as diaphragm switches comprising each a printed circuitry in an arrangement between two carrier foils within a fluid-tight hollow of the foot switch an extremely flat design structure of a very high trip safety and also of a respectively high step safety. The foot switch may be simply manufactured at low costs with a minimum malfunction even when the foot switch is designed with multiple press switches for controlling multiple functions via a common signalling line extending between the hollow of the foot switch and different functional members of the dental apparatus. A certainly safe operation of such multiple functional members will thereby be obtained with a differently dominating arrangement of the press switches over the actuating field of the cover plate of the foot switch.

Other objects, features and advantages of the present invention will become apparent from reading the following description of a preferred embodiment of a foot switch according to the present invention.

BRIEF DESCRIPTION OF THE DRAWING

FIG. 1 is a top view of the foot switch.

FIG. 2 is a sectional view of the foot switch along the line A—A in FIG. 1.

FIG. 3 is a sectional view of the foot switch along the line B—B in FIG. 1.

FIG. 4 is a perspective explosion view of the foot switch.

FIG. 5 is an enlarged view of the detail X in FIG. 4.

FIG. 6 is a top view of a printed circuit of the foot switch.

FIG. 7 is an inner view of the cover plate of the foot switch.

DETAILED DESCRIPTION

As shown by the top view in FIG. 1 a foot switch in accordance with the present invention is provided with a substantially elliptic to rectangular shape for housing a total of four electric press switches which are arranged for example for being used with a dental apparatus having a multifunctional dental handpiece which is connected with an ultrasonic power source.

The foot switch which is designated by the numeral 1 comprises a base plate 2 for supporting the foot switch on the floor at a location close to a dental apparatus which is operatively connected with the foot switch. The base plate 2 is covered by a relatively movable cover plate 3 which comprises a flexible-elastic material such as a preferred rubber-elastic material. The cover plate is fixedly connected along an edge portion with the base plate 2 in a fluid-tight manner. A space between the base plate 2 and the cover plate 3 provides a fluid-tight hollow 4. The base plate 2 is underlaid with a rubber nap plate for a slip-safe-support of the foot switch on the floor.

The hollow 4 between the base plate 2 and the cover plate 3 is used for the arrangement of multiple press switches. Two first and second press switches 5 and 6 are arranged in a major axis 7 of the foot switch 1. To further press switches 8 and 9 are arranged in a minor axis 10 of the foot switch whereby press switch 9 is designed as a double switch.

In accordance with the illustration in FIG. 5 all press switches are formed as diaphragm switches comprising each a printed circuitry in an arrangement on a first carrier foil 11 which is fixedly connected along an edge portion with a second carrier foil 12 in a fluid-tight manner. The package of these two carrier foils comprising the multiple press switches is arranged in the hollow 4 between the base plate 2 and the cover plate 3 whereby the cover plate 3 is provided with dome-shaped actuating projections 13, 14 and 15, 16 at the locations of the press switches. These actuating projections will therefore allow a separate actuation of all press switches. It should be noted that the projections 13 and 14 have substantially the same size and are less dominant than the projections 15 and 16 which are further provided with a different design.

When the foot switch is used for a dental apparatus comprising a multifunctional dental handpiece which is connected with an ultrasonic power source press switch 5 would then for example be arranged for controlling the ultrasonic power drive of the handpiece without any supply of water. On the other side press switch 6 would be arranged for controlling a rinsing with water of a preparation field of the teeth during a dental treatment whereby supply of water to the handpiece will be effected without any concurrent ultrasonic power drive. Press switch 8 which accordingly will be arranged at the location of the more dominant actuating projection 15 of a larger size than the two actuating projections 13 and 14 would be provided for controlling an ultrasonic power drive of the handpiece in combination with a supply of water to the handpiece. And press switch 9 would finally be arranged at the location of the also differently shaped actuating projection 16 for controlling a so-called boost ultrasonic operation of the handpiece with a regulated boost drive of the handpiece.

The printed circuits of the press switches are arranged for meeting at a common connection 17 for a signalling line 18 which directly connects to electric or electronic control systems of the different functional members of the dental apparatus which may be controlled by a depression of the different actuating projections of the cover plate 3 for actuating each of the press switches. At each location of an actuating projection there is further provided a contact spring 19 with an arrangement between the two carrier foils 11 and 12 which when an actuating projection is depressed will be moved from an inactive rest position to an active switch position.

The contact springs 19 are designed as disk-shaped click springs supplying an audible click noise when actuated upon depression of an associated actuating field of the cover plate 3 for actuating the associated press switch. When the depression is stopped the click springs will return to their rest position. For avoiding any over-load of the press switches each dome-shaped actuating projection comprises on its inner side a first actuating field 20 inside of an inner ring-shaped area through which the associated contact spring of the associated press button may be actuated. It further comprises a second actuating field 21 inside of a concentric outer ring-shaped area which when in contact with the base plate 2 of the foot switch 1 provides an overload protection for the associated press switch.

As noted above the foot switch 1 according to the present invention is provided with a substantially elliptic to rectangular shape. Press switches 5 and 6 which are arranged in the major axis 7 therefore provide less dominant actuating fields of the cover plate 3 by their associated projections 13 and 14 in comparison with the press switches 8 and 9 which are arranged in the minor axis 10. The more dominant actuating fields for the press switches 8 and 9 are further underlined by the larger design of the actuating projections 15 and 16 by comparison also with the same size of the smaller projections 13 and 14 which are arranged over the associated press switches 5 and 6 in the major axis 7 of the foot switch. By arranging these press switches 5 and 6 in the major axis of the foot switch a sufficiently large distance between these press switches and the press switches 8 and 9 of the minor axis 10 will be obtained to thereby secure a safe actuation of all four press switches for avoiding erroneous control functions of the interconnected handpiece.

The foot switch can also be provided for being used with a dental abrasive blasting apparatus in which case a first press switch would be arranged for activating a combined working jet of compressed air, abrasive powder particles and water for being discharged from a nozzle arrangement of a nozzle piece at a tip portion of an interconnected dental handpiece. A second press switch would be arranged for controlling a boost of a pressure of the combined working jet, a third press switch would be arranged for controlling a discharge only of compressed air and a fourth press switch would finally be arranged for controlling a discharge of compressed air in combination with water. The foot switch could also be used for controlling a dental drilling drive comprising similar control functions.

The arrangement of the multiple press switches within the hollow of the foot switch could further be supplemented by an arrangement of electrical load-sensing devices or load cells which are known per se and may comprise for example an electric resistor which will supply functional control signals that are proportionally dependent on the load acting on the cover plate of the foot switch for establishing a manipulated analog variable or control output of an associated functional member of the dental apparatus. Design examples for such load-sensing devices or load cells are for example electric conductive elastomer elements or foamed materials as well as piezoelectric ceramic disks or piezoelectric polymer foils which are connected with electronic load boosters.

I claim:

1. A foot switch for being operatively connected with a dental apparatus for operation of at least two different functional members of said dental apparatus, said foot switch comprising:

a base plate for supporting the foot switch on the floor, a cover plate which is movable relative to the base plate and fixedly connected along an edge portion with the base plate for forming a fluid-tight hollow between the base plate and the cover plate, a signaling line for being extended between the hollow and the at least two different functional members of the dental apparatus for transmitting functional control signals upon depression of the cover plate, the hollow housing at least two press switches which are electrically connectable via the signaling line with electrical or electronic switches of the at least two different functional members of the dental apparatus, the at least two press switches being each formed as diaphragm switches comprising each a printed circuitry with an arrangement between two carrier foils that are mutually fixed along an edge portion in a fluid-tight manner and supported on the base plate of the foot switch, each printed circuitry of a press switch comprising a contact spring which is arranged between the two carrier foils for triggering a functional control signal for an associated functional member of the dental apparatus upon depression of the cover plate at the location of the associated press switch.

2. The foot switch according to claim 1, wherein the cover plate is formed with at least two dome shaped actuating projections at the locations of the at least two press switches.

3. The foot switch according to claim 2, wherein the at least two dome-shaped actuating projections of the cover plate are of a different height.

4. The foot switch according to claim 2, wherein each dome-shaped actuating projection comprises a first actuating field inside of an inner ring-shaped area through which the contact spring of the associated press button may be actuated and a second actuating field inside of a concentric outer ring-shaped area which when in contact with the base plate of the foot switch provides an overload protection for the associated press switch.

5. The foot switch according to claim 1, wherein the cover plate comprises a flexible elastic material which is fixed along an edge portion to the base plate of the foot switch in a fluid-tight manner.

6. The foot switch according to claim 1, wherein each contact spring comprises a disk-shaped click spring which supplies an audible click noise when actuated upon depression of an associated actuating field of the cover plate of the foot switch for an actuation of the associated press button and which returns automatically to its unloaded rest position when the depression of the cover plate at the location of the associated press button is stopped.

7. The foot switch according to claim 1, wherein at least one electrical load-sensing device is arranged in the hollow of the foot switch in addition to the at least two press switches or alternatively which load-sensing device comprises an electric resistor supplying a functional control signal which is proportionally dependent on the load acting on the cover plate of the foot switch for establishing a manipulated analog variable or controller output of an associated functional member of the dental apparatus.

8. The foot switch according to claim 7, wherein the load-sensing device comprises electric conductive elastomer elements or foamed materials.

9. The foot switch according to claim 7, wherein said load-sensing device comprises piezoelectric ceramic discs or piezoelectric polymer foils which are connected with electronic load boosters.

10. The foot switch according to claim 1, for use with a dental apparatus comprising a multifunctional dental handpiece, wherein the foot switch is provided with four press switches of which a first press switch is arranged for controlling a first characteristic function of two definite functional actuating shares of the dental apparatus, a second press switch is arranged for controlling a regulating boost function, a third press switch is arranged for controlling only a first functional actuating share and a fourth press switch is arranged for controlling only a second functional actuating share of the characteristic function of the dental apparatus.

11. The foot switch according to claim 10, wherein said first and second press switches are associated with two dominant actuating fields of the cover plate of the foot switch and said third and fourth press switches are associated with two less dominant actuating fields at mutually offset locations of the cover plate.

12. The foot switch according to claim 11, wherein said dominant actuating fields of the first and second press switches are arranged in a minor axis and said less dominant actuating fields of the third and fourth press switches are arranged in a major axis of a substantially elliptic to rectangular shape of the foot switch.

13. The foot switch according to claim 12, wherein the dominant actuating fields of the first and second press switches are of a different size and of an ergonomically different form.

14. The foot switch according to claim 10, wherein the less dominant actuating fields of the third and fourth press switches are of the same size and are smaller than the actuating fields of the first and second press switches.

15. The foot switch according to claim 10, for use with a dental apparatus comprising a dental handpiece which is connected with an ultrasonic power source, wherein the first press switch is arranged for controlling an ultrasonic power drive of the handpiece in combination with a supply of water to the handpiece, the second press switch is arranged for controlling a so-called boost ultrasonic operation with a regulated boost drive of the handpiece, the third press switch is arranged for controlling an ultrasonic power drive of the handpiece without any supply of water and the fourth press switch is arranged for controlling a rinsing of a treated preparation field of the teeth during a dental treatment with water as supplied to the handpiece without any concurrent ultrasonic power drive of the handpiece.

16. The foot switch according to claim 10, for use with a dental abrasive blast apparatus, wherein the first press switch is arranged for activating a combined working jet of compressed air, abrasive powder particles and water for being discharged from a nozzle arrangement of a nozzle piece at a tip portion of an interconnected dental handpiece, the second press switch is arranged for controlling a boost of the pressure of the combined working jet, the third press switch is arranged for controlling a discharge only of compressed air and the fourth press switch is arranged for controlling a discharge of compressed air in combination with water.

17. A foot switch in combination with at least two different functional members of a dental apparatus which are operatively connected with the foot switch, comprising:

a) a base plate for supporting the foot switch on the floor at a location within a working distance of the dental apparatus, b) a cover plate which is movable relative to the base plate and fixedly connected along an edge portion with the base plate for forming a fluid-tight hollow between the base plate and the cover plate, c) a signalling line which extends between the hollow and the at least two different functional members of the dental apparatus for transmitting functional control signals upon depression of the cover plate, and d) at least two press switches which are electrically connected via the signalling line with electrical or electronic switches of said at least two different functional members of the dental apparatus, wherein e) said hollow is adapted for housing said at least two press switches, f) said at least two press switches being each formed as diaphragm switches comprising each a printed circuitry with an arrangement between two carrier foils that are mutually fixed along an edge portion in a fluid-tight manner and supported on the base plate of the foot switch, and wherein g) each press switch comprises a contact spring which is arranged between the two carrier foils for triggering a functional control signal for an associated functional member of the dental apparatus upon depression of the cover plate at the location of the contact spring which moves said contact spring from an inactive rest position to an active switch position.

* * * * *